US010653320B2

(12) United States Patent
Trovato et al.

(10) Patent No.: US 10,653,320 B2
(45) Date of Patent: May 19, 2020

(54) VOLUME MAPPING USING OPTICAL SHAPE SENSORS (71) Applicant: KONINKLIJKE PHILIPS N.V., Eindhoven (NL)

(72) Inventors: Karen Irene Trovato, Putnam Valley, NY (US); Raymond Chan, San Diego, CA (US); Robert Manzke, Bönebüttel (DE); Cynthia Ming-fu Kung, New York, NY (US); Bharat Ramachandran, Morganville, NJ (US); Laurent Verard, Katonah, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 492 days.

(21) Appl. No.: 14/430,688

(22) PCT Filed: Sep. 20, 2013

(86) PCT No.: PCT/IB2013/058687
§ 371 (c)(1),
(2) Date: Mar. 24, 2015

(87) PCT Pub. No.: WO2014/053941
PCT Pub. Date: Apr. 10, 2014

(65) Prior Publication Data
US 2015/0238275 A1 Aug. 27, 2015

Related U.S. Application Data (60) Provisional application No. 61/708,768, filed on Oct. 2, 2012.

(51) Int. Cl.
A61B 8/00 (2006.01)
A61B 5/00 (2006.01)
(Continued)

(52) U.S. Cl.
CPC ........ *A61B 5/0084* (2013.01); *A61B 5/02055* (2013.01); *A61B 5/1073* (2013.01);
(Continued)

(58) Field of Classification Search
CPC . A61B 19/5244; A61B 5/6843; A61B 5/6858; A61B 5/0084
See application file for complete search history.

(56) References Cited

U.S. PATENT DOCUMENTS 5,255,678 A 10/1993 Deslauriers et al.
5,263,493 A 11/1993 Boaz
(Continued)

FOREIGN PATENT DOCUMENTS

JP 2012090690 A 5/2012
WO 2007022986 A2 3/2007
(Continued)

*Primary Examiner* — Joseph M Santos Rodriguez (57) ABSTRACT

A volume mapping instrument (20), deployable within a partially or a completely enclosed anatomical volume, employs one or more medical tools (40) with each medical tool (40) being transitional between a deployable structural configuration to orderly position each medical tool (40) within the anatomical volume and a mapping structural configuration to anchor the medical tool (40) against the boundary of the anatomical volume. The volume mapping instrument (20) further employs an optical shape sensor (30) to generate one or more encoded optical signals indicative of a shape of the boundary of the anatomical volume in response to each medical tool (40) being transitioned from the deployable structural configuration to the mapping structural configuration within the anatomical volume. Based on the encoded optical signal(s), a volume mapping module (51) is utilized to map a portion or an entirety of the boundary of the anatomical volume.

9 Claims, 6 Drawing Sheets (51) Int. Cl.
    *A61B 5/107*     (2006.01)
    *A61B 34/20*     (2016.01)
    *A61B 5/0205*     (2006.01)
    *A61B 90/00*     (2016.01)

(52) U.S. Cl.
    CPC .......... *A61B 5/1076* (2013.01); *A61B 5/6853* (2013.01); *A61B 5/6858* (2013.01); *A61B 34/20* (2016.02); *A61B 5/6857* (2013.01); *A61B 90/06* (2016.02); *A61B 2034/2051* (2016.02); *A61B 2034/2061* (2016.02); *A61B 2090/063* (2016.02); *A61B 2562/0266* (2013.01); *A61B 2562/043* (2013.01)

(56) References Cited

U.S. PATENT DOCUMENTS

| | | | |
|---|---|---|---|
| 5,465,717 A * | 11/1995 | Imran | A61B 5/0422 600/374 |
| 5,752,518 A | 5/1998 | McGee et al. | |
| 6,192,266 B1 * | 2/2001 | Dupree | A61B 5/0422 600/427 |
| 6,868,195 B2 | 3/2005 | Fujita | |
| 7,522,950 B2 | 4/2009 | Fuimaono | |
| 8,417,491 B2 | 4/2013 | Trovato et al. | |
| 2008/0008369 A1 | 1/2008 | Koptenko et al. | |
| 2009/0248045 A1 | 10/2009 | Trovato | |
| 2009/0324161 A1 | 12/2009 | Prisco | |
| 2010/0030063 A1 * | 2/2010 | Lee | A61B 5/06 600/424 |
| 2012/0197097 A1 | 8/2012 | Chan et al. | |
| 2013/0150693 A1 * | 6/2013 | D'Angelo | A61B 5/036 600/373 |
| 2013/0150732 A1 | 6/2013 | Manzke et al. | |
| 2014/0222370 A1 | 8/2014 | Manzke et al. | |
| 2015/0238275 A1 | 8/2015 | Kung et al. | |

FOREIGN PATENT DOCUMENTS

| | | | |
|---|---|---|---|
| WO | 2010111090 A1 | 9/2010 | |
| WO | WO 2012025856 A1 * | 3/2012 | ....... A61B 17/00234 |

* cited by examiner

VOLUME MAPPING USING OPTICAL SHAPE SENSORS

CROSS-REFERENCE TO PRIOR APPLICATIONS

This application is the U.S. National Phase application under 35 U.S.C. § 371 of International Application Serial No. PCT/IB2013/058687, filed on Sep. 20, 2013, which claims the benefit of U.S. Application Ser. No. 61/708,768, filed on Oct. 2, 2012. These applications are hereby incorporated by reference herein.

FIELD OF THE INVENTION

The present invention generally relates to an optical shape sensor being anchored by one or more medical tools (e.g., balloons, baskets, shape memory tubes, etc.) within a partially or completely bounded anatomical volume to sense a three-dimensional ("3D") shape of a portion or an entirety of the boundary of the anatomical volume. The present invention specifically relates to mapping the 3D shape of a portion or an entirety of the bounded anatomical volume based on the shape sensing capabilities of the optical shape sensor and if applicable, the physical geometry of the medical tool(s).

BACKGROUND OF THE INVENTION

As known in the art, an imaging system may be utilized to implement a known imaging modality (e.g., X-ray, computed tomography, magnetic resonance imaging, ultrasound, positron emission tomography and single-photon emission computed tomography) for generating images of a targeted organ of a patient (e.g., a potentially cancerous organ or an abnormally functioning organ). These images may be utilized by a physician for diagnosis of the patient and/or to plan and execute various treatments of the organ (e.g., image-guided surgery, radiation therapy, etc.). To facilitate an accurate treatment plan for the targeted organ, the targeted organ may need to be segmented for identification and visualization of a contour of the targeted organ within the images.

However, because the image may be difficult to read such as if metal obscures or interferes the anatomy, identification and visualization of the contour of the targeted organ within the image may be impossible or error-prone. Image segmentation typically requires a highly-trained physician to select various points on the surface of the targeted organ to electronically paint the contour of the targeted organ. This can be time consuming and prone to error. More particularly, a demarcation of the boundary between an organ and internal fluids may be difficult due to poor visualization of the organ. A contrast material may be used to help highlight particular anatomy, although some people are sensitive to the contrast.

Alternatively, an automatic segmentation program may be utilized, such as, for example, a boundary reparameterization method disclosed by U.S. Patent Application Publication 20080008369 A1. However, as recognized by the aforementioned publication, the boundaries of the targeted organ may be difficult to identify for various reasons including being masked by the presence of speckle noise, appearing weak in the images due to shading by overlying features and false edges formed by two regions of different gray levels or as the edge between two different textures, or as a hybrid of the two. This complexity leads to high failure rates for image-based automatic segmentation algorithms.

SUMMARY OF THE INVENTION

An objective of the present invention is to provide a mapping method to measure shape of the anatomical volume (e.g., hollow organs) and to optionally measure various parameters including, but not limited to, motion, strain, magnetism, voltage, gas flow, fluid flow, temperature, pressure, biochemical state and any other characteristics related to the intrinsic tissue properties or response of tissue to extrinsic factors. Particularly, the shape/parameter measurements may occur over time to thereby produce four-dimensional ("4D") information of the anatomical volume. To this end, the present invention provides for an optical shape sensor being orderly positioned and anchored within a partially or a completely bounded volume by medical tool(s) to map a three-dimensional ("3D") shape of a portion or an entirety of the boundary of the volume.

One form of the present invention is a volume mapping instrument deployable within an anatomical volume for mapping a portion or an entirety of a boundary of the anatomical volume. The volume mapping instrument employs one or more medical tools with one or each medical tool being transitional between a deployable structural configuration to orderly position the medical tool(s) within the anatomical volume and a mapping structural configuration to anchor one or each medical tool against the boundary of the anatomical volume.

Examples of the medical tool(s) include, but are not limited to, (1) a medical balloon transitional between a deflated compressed state and an inflated expanded state, (2) a medical basket including shape memory material for transitioning the medical basket between an elongated shape and a spherical shape, and (3) a medical tube including shape memory material for transitioning the medical tube between an elongated shape and a helical shape.

The volume mapping instrument further employs an optical shape sensor adjoined to the medical tool(s) with the optical shape sensor being structurally configured to generate one or more encoded optical signals indicative of a shape of a portion or an entirety of the boundary of the anatomical volume in response to one or each medical tool being transitioned from the deployable structural configuration to the mapping structural configuration within the anatomical volume.

A second form of the present invention is a volume mapping system employing the aforementioned volume mapping instrument and further employing a volume mapping module to map the portion or the entirety of the boundary of the anatomical volume based on the encoded optical signal(s).

A third form of the present invention is a volume mapping method for utilizing the aforementioned volume mapping system. The volume mapping method involves an orderly positioning of one or each medical tool within the anatomical volume and an anchoring of one or each medical tool as positioned within the anatomical volume against the boundary of the anatomical volume. The volume method further involves, in response to one or each medical tool being anchored against the boundary of the anatomical volume, an operation of the optical shape sensor to generate one or more encoded optical signals indicative of a shape of the portion or the entirety of the boundary of the anatomical volume, and a mapping of the portion or the entirety of the boundary of the anatomical volume based on the encoded optical signal(s).

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF EMBODIMENTS

Figure 1:
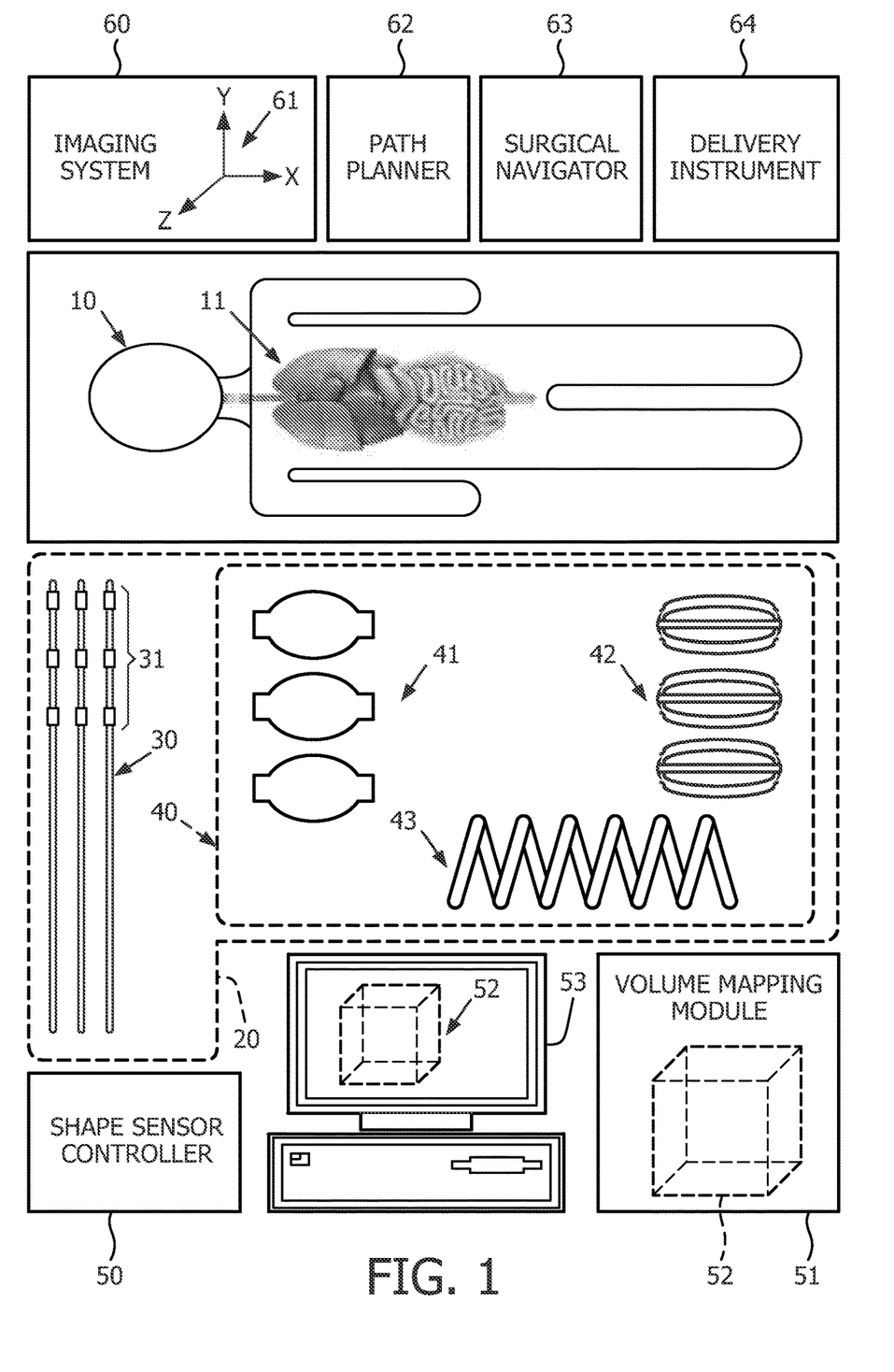
FIG. 1 illustrates an exemplary embodiment of a volume mapping system in accordance with present invention.

FIG. 1 illustrates a volume mapping instrument 20 of the present invention employing one or more optical shape sensors 30, and one or more medical tools 40. Generally, for purposes of mapping a partially or a completely enclosed anatomical volume, each optical shape sensor 30 is orderly positioned and anchored within the bounded anatomical volume by medical tool(s) 40 to map a three-dimensional ("3D") shape of a portion or an entirety of the boundary of the anatomical volume and to optionally measure various parameters including, but not limited, motion, strain, magnetism, voltage, gas flow, fluid flow, temperature, pressure, biochemical state and any other characteristics related to the intrinsic tissue properties or response of tissue to extrinsic factors. Examples of the anatomical volume include, but are not limited to, hollow organs 11 of a patient 10 as shown in FIG. 1 consisting of a heart, lungs, bladder, stomach, intestines, uterus and colon.

Specifically, for purposes of the present invention, an optical shape sensor 30 is broadly defined herein as any article structurally configured for transmitting light by means of successive internal optical reflections via a deformation optic sensor array 31, and each deformation optic sensor of the array 31 is broadly defined herein as any article structurally configured for reflecting a particular wavelength of light while transmitting all other wavelengths of light whereby the reflection wavelength may be shifted as a function of an external stimulus applied to the optical shape sensor 30. Examples of optical shape sensor 30 include, but are not limited to, a flexible optically transparent glass or plastic fiber incorporating an array of Fiber Bragg Gratings integrated along a length of the fiber as known in the art, and a flexible optically transparent glass or plastic fiber having naturally random variations in its optic refractive index occurring along a length of the fiber as known in the art (e.g., Rayleigh scattering).

While only three (3) sensors 31 are shown for each optical fiber 30 for clarity, in practice optical fibers 30 will employ a smaller version of sensors 31 in multitude relative to the length of an optical fiber 30 as will be appreciated by those having ordinary skill in the art.

In practice, each optical shape sensor 30 may employ one or more deformation optic sensor arrays in any arrangement that facilitates 3D bend sensing of optical shape sensor 30.

For example, in a single optic fiber embodiment, an optical shape sensor 30 is a single optical fiber having three (3) Fiber Bragg Grating arrays arranged at 120° spacing as required for 3D bend sensing by optical shape sensor 30 or having six (6) Fiber Bragg Grating arrays arranged at 60° spacing as required for 3D bend sensing by optical shape sensor 30. In either case, an additional Fiber Bragg Grating array may be employed as a central Fiber Bragg Grating array within the arrangements.

Also by example, in a multi-optic fiber embodiment, an optical shape sensor 30 includes three (3) optical fibers with each optical fiber having a single fiber Bragg grating array and the optical fibers are arranged at 120° spacing as required for 3D bend sensing by optical shape sensor 30 or includes six (6) optical fibers with each optical fiber having a single fiber Bragg grating array and the optical fibers are arranged at 60° spacing as required for 3D bend sensing by optical shape sensor 30. In either case, an additional optical fiber may be employed as a central optical fiber within the arrangements.

In operation, each optical shape sensor 30 generates an encoded optical signal for each deformation optic sensor array based on the successive internal optical reflections that indicates a shape of the optical shape sensor 30 at any instantaneous shape sampling of the optical shape sensor 30. More particularly, for an instantaneous shape sampling or over the course of multiple shape samplings, the encoded optical signal indicates the shape of optical shape sensor 30 as an optical shape sensor 30 is orderly positioned and anchored within the bounded volume by medical tool(s) 40. The encoded optical signal therefore facilitates a use of each optical shape sensor 30 for mapping a boundary of the volume (e.g., mapped volume 52 of heart 12 as shown in FIG. 1) as will be subsequently explained in more detail herein and for visually displaying the mapped volume (e.g., display 53 of mapped volume 52 as shown in FIG. 1).

For parameter measurement, deformation optic sensor array 31 may be composed of and/or coated with materials that provide for such measurement as taught by WO 2011048509, incorporated herein by reference. Examples of such materials include, but are not limited to, $Bi_{12}TiO_{20}$ crystals for voltage sensing, Ni—Mn—Ga memory shape metal alloys for magnetic sensing, and Zn metal vapor depositions for enhanced temperature sensing.

For purposes of the present invention, a medical tool 40 is broadly defined herein as any article structurally configured to be transitional between a deployable structural configuration to orderly position the medical tool 40 within an anatomical volume and a mapping structural configuration to anchor the medical tool 40 against the boundary of the anatomical volume. Examples of a medical tool 40 include, but are not limited to, a medical balloon 41 transitional between a deflated compressed state and an inflated expanded state, a medical basket 42 including shape memory material for transitioning the medical basket between a deformed elongated shape and a natural spherical shape, and medical tube 43 including shape memory material for transitioning the medical tube between a deformed elongated shape and a natural helical shape.

Each optical shape sensor 30 is adjoined to the medical tool(s) 40 in a manner than facilitates an orderly positioning and anchoring within the bounded anatomical volume by medical tool(s) 40 to map the 3D shape of a portion or an entirety of the boundary of the anatomical volume. For purposes of the present invention, the term "adjoined" is broadly defined as any means for physically interfacing optical shape sensor 30 to a medical tool 40 whereby a transition between the deployable structural configuration and the mapping structural configuration of the medical tool 40 is sensed by the optical shape sensor 30 as an external stimulus applied to optical shape sensor 30 during the transitions.

Figure 2A:
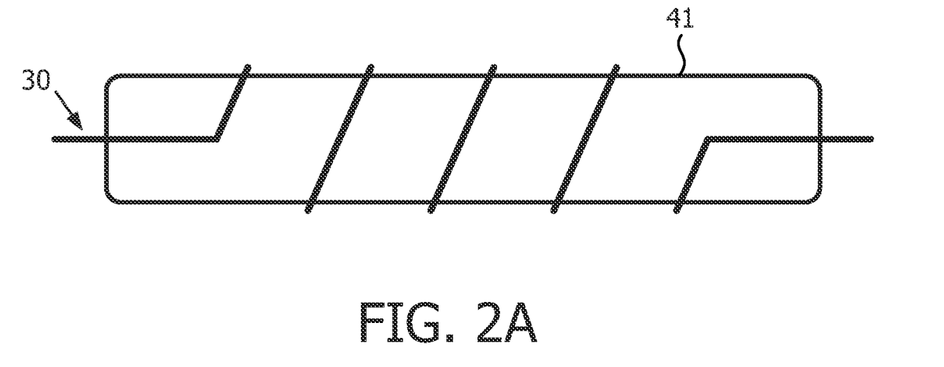
FIGS. 2A and 2B illustrate an exemplary embodiment of a volume mapping instrument having a medical balloon in a deflated state and an inflated state, respectively, in accordance with the present invention.
Figure 2B:
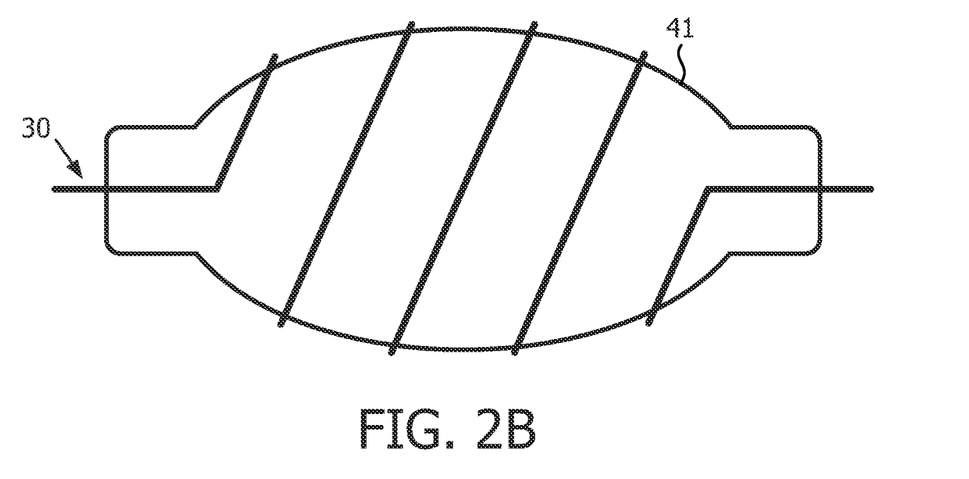
Figure 3:
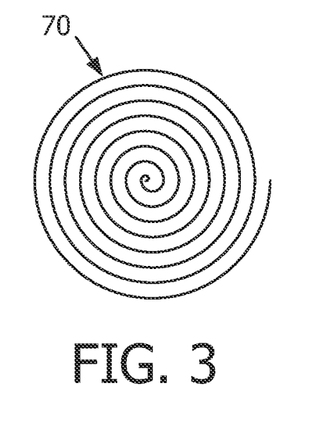
FIG. 3 illustrates a first exemplary embodiment of a spiral configuration of an optical fiber adjoined to the medical balloon shown in FIGS. 2A and 2B.
Figure 4:
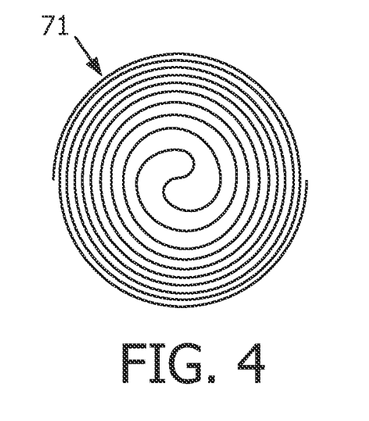
FIG. 4 illustrates a second exemplary embodiment of a spiral configuration of an optical fiber adjoined to the medical balloon shown in FIGS. 2A and 2B.

For example, in a medical balloon embodiment as shown in FIG. 2, an optical shape sensor 30 traverses a medical balloon 41 in a spiral pattern whereby a transition of medical balloon 41 between a deflated state (FIG. 2A) and an inflated state (FIG. 2B) is sensed by the optical shape sensor 30 as a compression or an expansion of medical balloon changes an external stimulus applied to optical shape sensor 30. In practice, optical shape sensor 30 in the designed spiral pattern may be adjoined to medical balloon 41 in a maximum inflated state for the volume mapping whereby the spiral pattern will corresponding compress with medical balloon 41 whenever medical balloon 41 is deflated to some degree from the maximum inflated state. Examples of the spiral pattern include, but art not limited to, a Spiral of Archimedes pattern 70 as shown in FIG. 3 and a Fermat's Spiral pattern 71 as shown in FIG. 4.

As will be subsequently explained herein in connection with FIG. 8, each medical balloon 41 will be operated in a deflated state as volume mapping instrument 20 is advanced into the anatomical volume via a delivery instrument 64 (FIG. 1) and will be transitioned to the inflated state within the anatomical volume. As such, optical shape sensor 30 will provide a deflated sensing of each medical balloon 41 until such time the medical balloon(s) 41 are inflated within the anatomical volume.

Figure 5A:
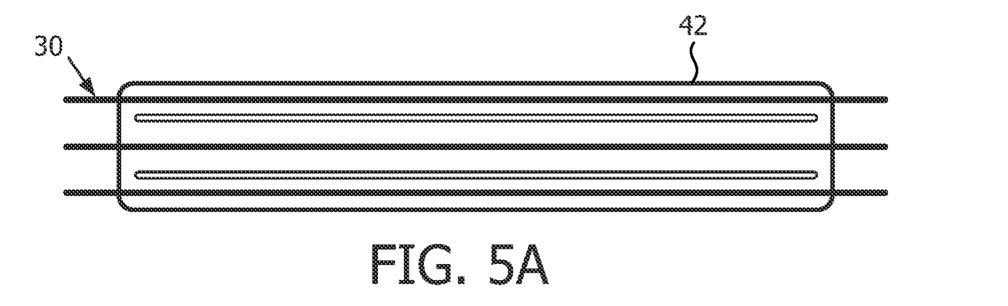
FIGS. 5A and 5B illustrate an exemplary embodiment of a volume mapping instrument having a medical basket with an elongated shape and a spherical shape, respectively, in accordance with the present invention.
Figure 5B:
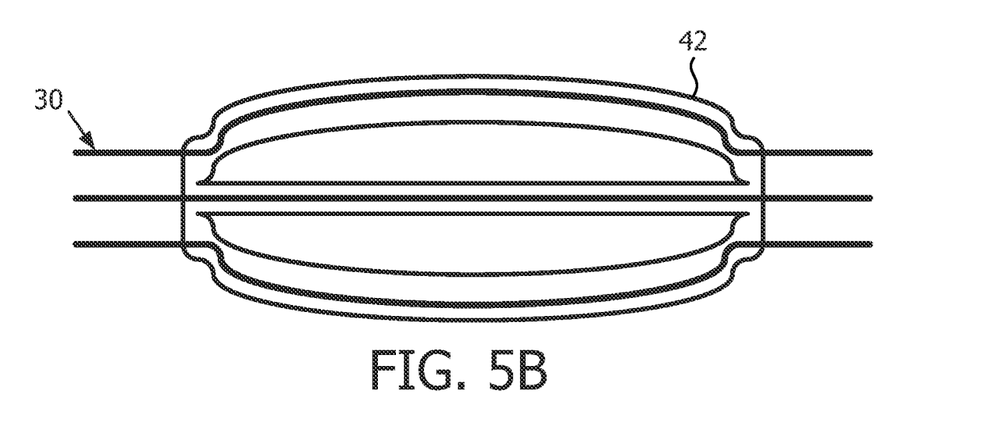

Also by example, in a medical basket embodiment as shown in FIG. 5, a medical basket 42 includes shape memory material (e.g., Nitinol wires) whereby medical basket 42 is transitional between a deformed elongated shape (FIG. 5A) and a natural spherical shape (FIG. 5B), and any transition between the elongated shape and the spherical shape is sensed by optical shape sensor 30 as a deformation or a relaxation of medical balloon changes an external stimulus applied to optical shape sensor 30. In practice, optical shape sensor 30 may be adjoined to medical basket 42 in the natural spherical shape for the volume mapping whereby the optical shape sensor 30 will locally elongate whenever medical basket 42 is deformed to some degree from the natural spherical shape.

As will be subsequently explained herein in connection with FIG. 8, each medical basket 42 will be operated in a deformed elongated shape as volume mapping instrument 20 is advanced into the anatomical volume via a delivery instrument 64 (FIG. 1) and will be transitioned to the natural spherical shape within the anatomical volume. As such, optical shape sensor 30 will provide an elongated sensing of each medical basket 42 until such time the medical basket(s) 42 resume their natural spherical shape within the anatomical volume.

Figure 6A:
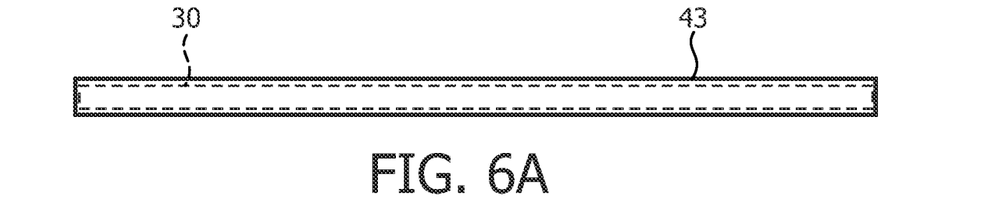
FIGS. 6A and 6B illustrate an exemplary embodiment of a volume mapping instrument having a medical tube with an elongated shape and a helical shape, respectively, in accordance with the present invention.
Figure 6B:
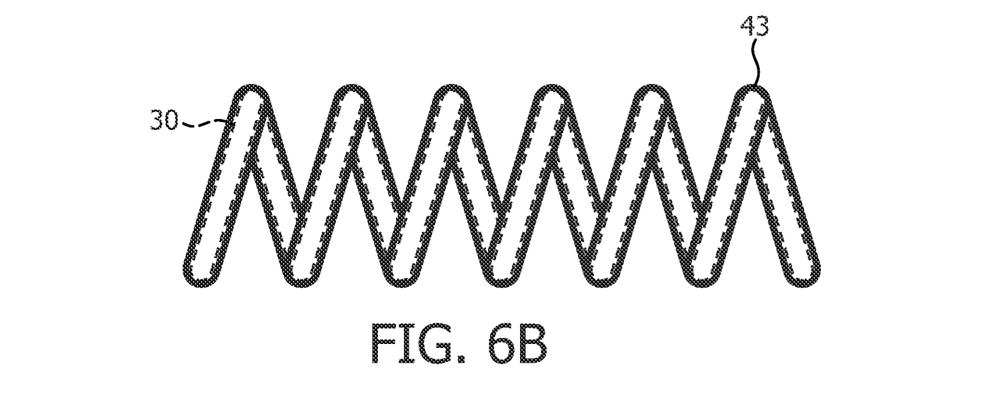

By further example, in a medical tube embodiment as shown in FIG. 5, a medical tube 43 includes shape memory material (e.g., Nitinol tubing) whereby medical tube 43 is transitional between a deformed elongated shape (FIG. 6A) and a natural helical shape (FIG. 6), and any transition between the elongated shape and the helical shape is sensed by optical shape sensor 30 as a deformation or a relaxation of medical balloon changes an external stimulus applied to optical shape sensor 30. In practice, optical shape sensor 30 may be adjoined to medical tube 43 in the natural helical shape for the volume mapping whereby the optical shape sensor 30 will locally elongate whenever medical tube 43 is deformed to some degree from the natural helical shape.

As will be subsequently explained herein in connection with FIG. 9, medical tube 43 will be operated in a deformed elongated shape as volume mapping instrument 20 is advanced into the anatomical volume via a delivery instrument 64 (FIG. 1) and will be transitioned to the natural helical shape within the anatomical volume. As such, optical shape sensor 30 will provide an elongated sensing of medical tube 42 until such time medical tube 43 resumes its natural helical shape within the anatomical volume.

To facilitate a further understanding of volume mapping instrument 20, a volume mapping method of the present invention as represented by a flowchart 80 shown in FIG. 7 will now be described herein. The description of flowchart 80 will be provided in the context of volume mapping a hollow lung 11 of patient 10 as shown in FIG. 1.

Figure 7:
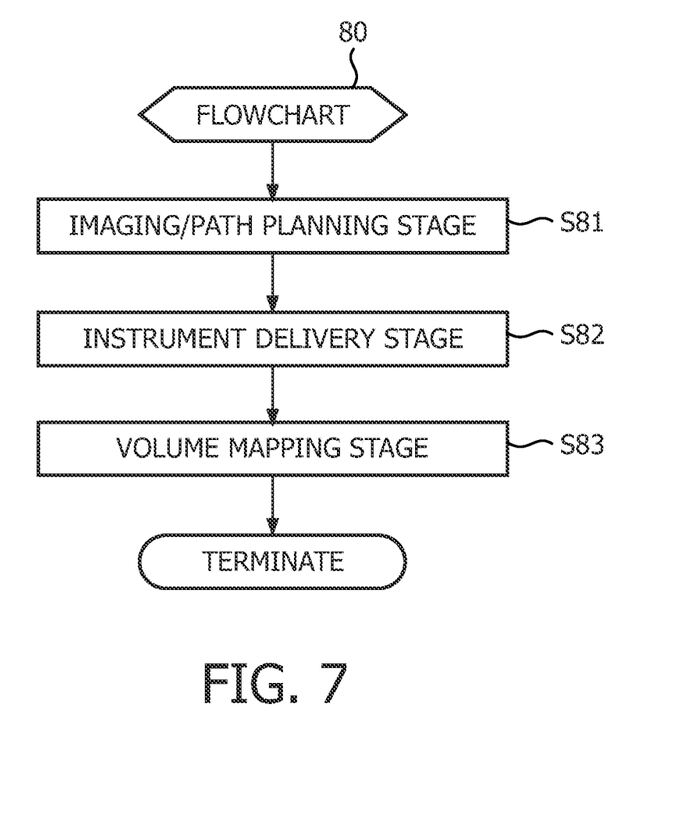
FIG. 7 illustrates an exemplary embodiment of a volume mapping method in accordance with the present invention.

Referring to FIGS. 1 and 7, a stage S81 of flowchart 80 encompasses an imaging of hollow organ 11 of patient 10 and a planning of a path to advance volume mapping instrument 20 to hollow organ 11. For imaging hollow organ 11, an imaging system 60 is utilized to implement a known imaging modality (e.g., X-ray, computed tomography, magnetic resonance imaging, ultrasound, positron emission tomography and single-photon emission computed tomography) for generating images hollow organ 11 within an imaging coordinate system 61.

For planning a path to advance volume mapping instrument 20 to hollow organ 11, path planner 62 and/or a surgical navigator 63 is(are) utilized to implement a known planning technique dependent upon the type of delivery instrument 64 to be utilized as the means for advancing volume mapping instrument 20 to hollow organ 11.

For example, in a context of delivery instrument 64 being a catheter or an endoscope, path planner 62 may implement a technique taught by International Application WO 2007022986 A2 to Trovato et al. published Apr. 17, 2007, and entitled "3D Tool Path Planning, Simulation and Control System" may be used to generate a kinematically correct path for the catheter or the endoscope within the generated image of patient 10.

Alternatively, in a context of delivery instrument 64 being a catheter or an endoscope, surgical navigator 62 may utilize electromagnetic or optical guidance system for tracking the catheter or the endoscope within the generated image of patient 10. An example of such a surgical navigator is PercuNav system commercially offered by Philips Medical that operates like a global positioning system ("GPS") for catheter and endoscopes.

Also by example, in the context of delivery instrument 64 being a nested cannula, the path planner 62 may implement a technique taught by International Application WO 2008032230 A1 to Trovato et al. published Mar. 20, 2008, and entitled "Active Cannula Configuration For Minimally Invasive Surgery" may be used to generate a kinematically correct configuration for the nested cannula within the generated image of patient 10.

A stage S82 of flowchart 80 encompasses an orderly positioning and anchoring of volume mapping instrument 20 within hollow organ 11. In practice, the procedure for delivering volume mapping instrument 20 to hollow organ 11 is dependent upon the type of medical tool 40 and delivery instrument 64. Two (2) examples will now be described herein.

Figure 8A:
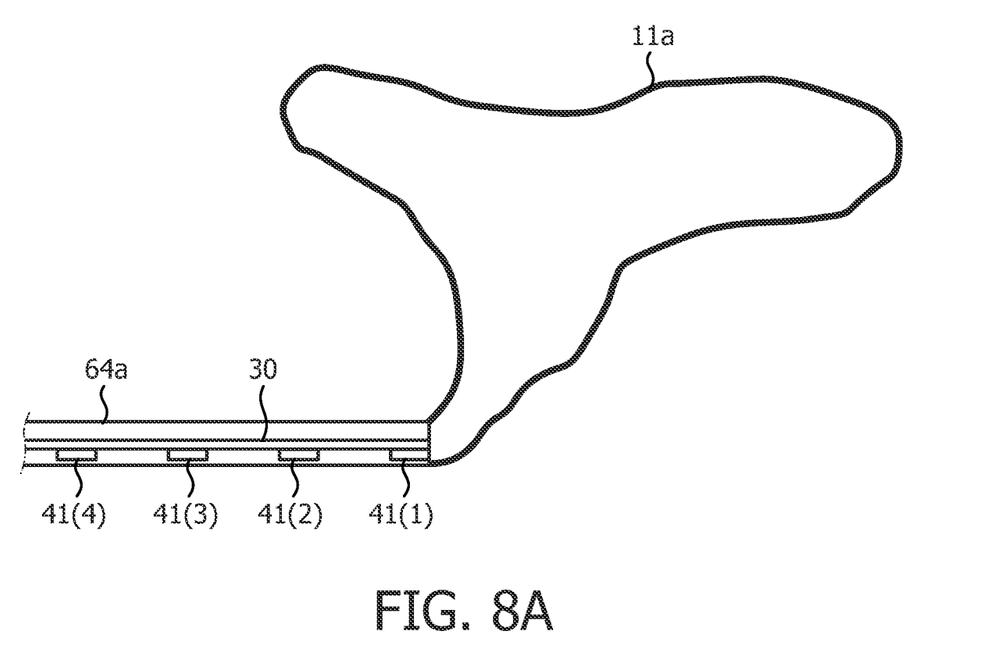
FIGS. 8A and 8B illustrate a first exemplary execution of a mapping of an anatomical volume in accordance with the flowchart shown in FIG. 7.
Figure 8B:
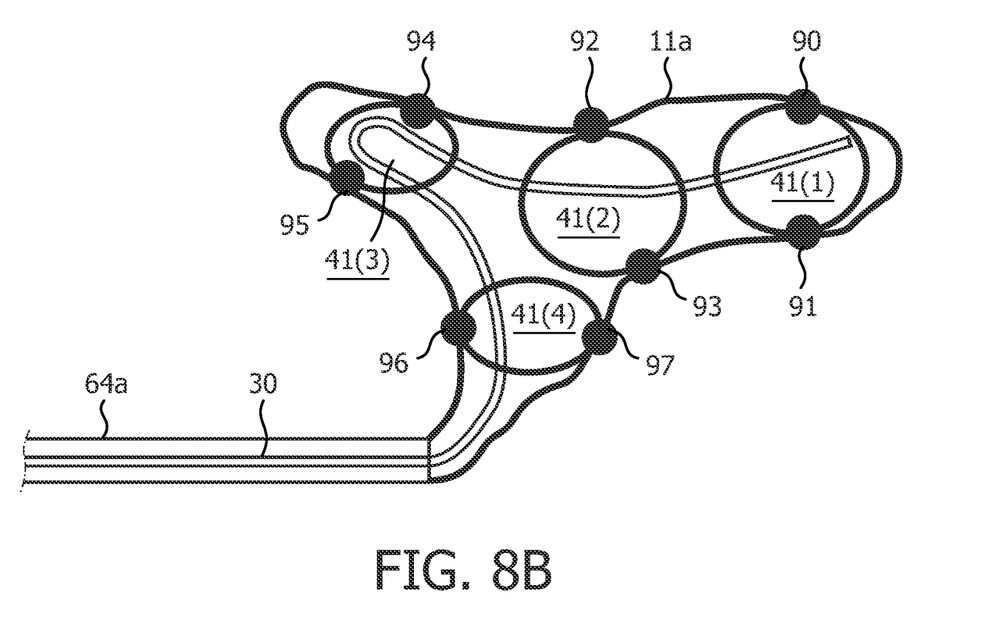

For the first example involving a generic boundary of a hollow organ 11a as shown in FIG. 8, medical tool 40 includes four (4) medical balloons 41 and delivery instrument 64 is a catheter 64a. Medical balloons 41 are spatially distributed along a distal end of a single optical shape sensor 30 and are in a compressed deflated state within catheter 64a. In one embodiment of optical shape sensor 30 having one or more optical fibers, each optical fiber optical shape sensor 30 may run through channels in the surface of each medical balloon 41 (with or without wall elements such as wire or polymer coil tube to keep the channels open) in a spiral pattern, that enables medical balloons 41 to expand while still allowing for shape tracking by the flexible, but relatively unstretchable, optical fibers. The termination of each optic fiber inside the pattern may constitute a fixed point, which is mechanically constrained in all directions within the flexible membrane, whereas the other points along the optical fibers are allow to slide freely with sliding boundary conditions parallel to the channel groove in the flexible matrix within which the optical fiber is embedded.

Furthermore, a loose length of each optic fiber may be attached at each end of one medical balloon 41 as it continues toward the medical balloon 41. The length is preferably between the shortest path length and distance over the expanded surface of each medical balloons 41. Since each medical balloon 41 will be compressed to some degree by hollow organ 11a other medical balloons 41, the path should indicate the size of the expanded medical balloon 41.

Please note optical shape sensor 30 is shown in FIG. 8B as longitudinally traversing across each medical balloon 41 to simplify FIG. 8B. Nonetheless, in practice, optical shape sensor 30 being arranged in a spherical pattern a shown in FIGS. 3 and 4 would provide an optimal sensing of the inflation of medical balloons 41.

Catheter 64a may be navigated to deliver the volume mapping instrument to a specific entrance point of hollow organ 11a as shown in FIG. 8A whereby the volume mapping instrument is advanced into hollow organ 11a in a designed pattern to facilitate an orderly positioning of the volume mapping instrument within hollow organ 11a, particularly medical balloons 41. Alternatively, catheter 64a may be advanced into hollow organ 11 in a designed pattern to facilitate to facilitate an orderly positioning of the volume mapping instrument within hollow organ 11, particularly medical balloons 41.

In either case, once medical balloons 41 are orderly positioned within hollow organ 11a, medical balloons 41 are inflated to anchor medical balloons 41 against the boundary of hollow organ 11a. In practice, medical balloons 41 may automatically triggered whereby the inflation is automatically initiated via a pneumatic actuator that takes as input measurements from embedded sensors within medical balloons 41 (e.g. temperature, strain, geometry, humidity, pO2, pCO2, etc.) to assess actuation criteria (e.g., depth of instrument insertion). Alternatively, the inflation of medical balloons 41 may be timed in a programmable or automated sequence to achieve the optimal fixation profile against the boundary of hollow organ 11a. With the trigger or the timer, medical balloons 41 may be inflated sequentially as each medical balloon 41 enter hollow organ 11a, or alternatively upon an insertion of two (2) or more of medical balloons 41.

Also in practice, imaging system 60 may be utilized to orderly position medical balloons 41 within hollow organ 11a and/or visualize an acceptable anchoring of medical balloons 41 against the boundary of hollow organ 11a.

Those having ordinary skill in the art will appreciate an alternate utilization of medical baskets 42 (FIG. 1) in lieu of medical balloons 41 for the example of FIG. 8.

Figure 9:
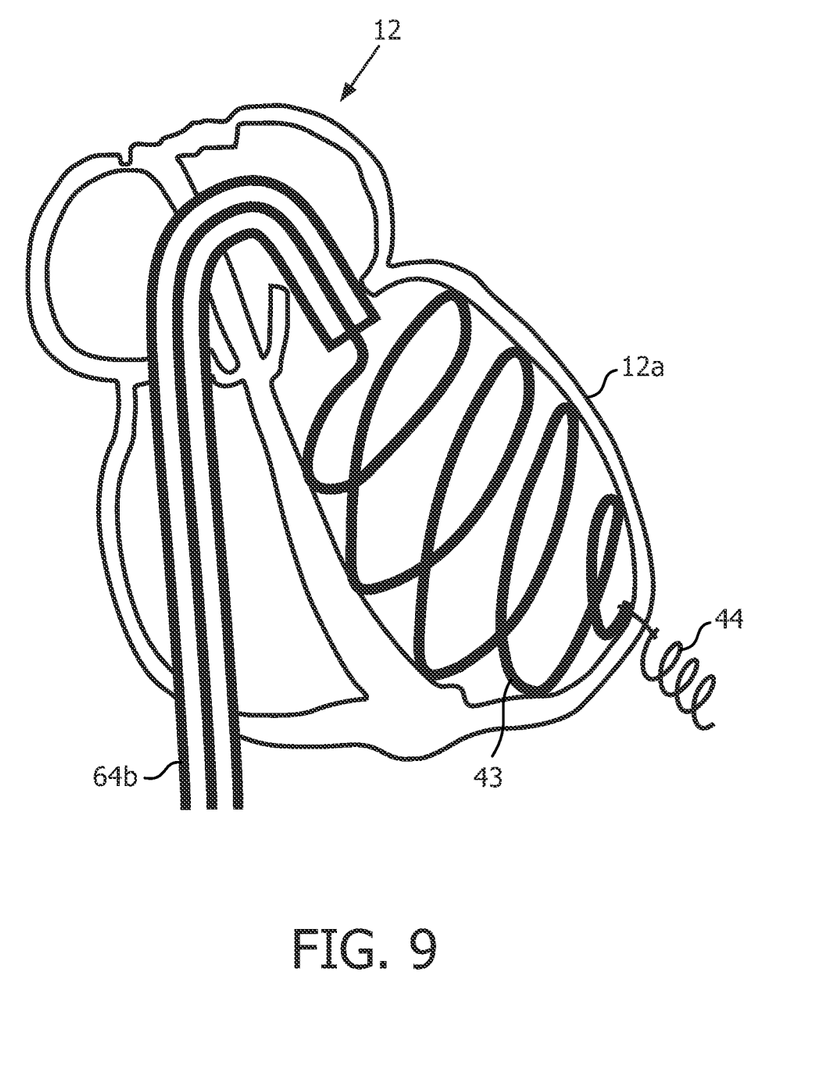
FIG. 9 illustrates a second exemplary execution of a mapping of an anatomical volume in accordance with the flowchart shown in FIG. 7.

For the second example involving a heart 12 as shown in FIG. 9, medical tool 40 is a helical tube 43 and delivery instrument is a cannula 64b. As shown in FIG. 6, optical shape sensor 30 with an elongated shape extends through helical tube 43, which extends in an elongated shape through cannula 64b. In this example, cannula 64b is longitudinally extended advanced into right atrium 12a of heart 12 and the volume mapping instrument is affixed to right atrium 12a via a coil 44. Cannula 64b is thereafter refracted to the opening of right atrium 12a as shown in FIG. 9, helical tube 43 and optical shape sensor 30 assume a natural helical shape of helical tube 43, and helical tube 43 anchors against the boundary of right atrium 12a.

Referring again to FIG. 7, a stage S83 of flowchart 80 encompasses a volume mapping of hollow organ 11 within the generated images. In practice, in view of the fact that optical shape sensor 30 may detect the position in 3D of optical shape sensor along its length within image coordinate system 62 (FIG. 1), the distribution of optic shape sensor 30 within hollow organ 11, the design of fixation points of optic shape sensor 30 via medical tool(s) 40, and a degree of fixity will be important mapping factors to consider for accurate mapping of hollow organ 11 as the medical tool(s) 41 are anchored against hollow organ 11.

Referring to FIG. 1, a shape sensor controller 50 and a volume mapping module 51 employed for processing an encoded optical signal of optical shape sensor 30 to thereby reconstruct a portion or an entire shape of optical shape sensor 30. For purposes of the present invention, shape sensor controller 50 is broadly defined herein as any device or system structurally configured for transmitting light through optical shape sensor 30 to receive the encoded optical signal as generated by the successive internal reflections of the transmitted light via deformation optic sensor array. An example of shape sensor controller 50 includes, but is not limited to, an arrangement of an optical coupler, a broadband reference reflector and a frequency domain reflectometer as known in the art for transmitting light through optical shape sensor 30 and for receiving the encoded optical signal as generated by the successive internal reflections of the transmitted light via deformation optic sensor array.

For purposes of the present invention, volume mapping module 52 includes a shape reconstructor that is broadly defined as any article or device structurally configured for processing the encoded optic signal to partially or entirely reconstruct the shape of optical shape sensor 30. An example of the shape reconstructor includes, but is not limited to, a reconstruction engine installed as software and/or firmware on any type of computer (e.g., workstation 53 shown in FIG. 1) for implementing a known shape reconstruction technique. In particular, a known shape reconstruction technique for correlating the encoded optic signal into strain/bend measurements that are integrated into a shape of optical shape sensor 30.

Volume mapping module 52 further includes an image mapper that is broadly defined as any article or device structurally configured for processing the reconstructed shape of optical shape sensor 21 and if applicable, the physical geometry of medical tool(s) 40 in the mapping structural configuration to provide the 3D shape of the boundary of hollow organ 11 within image coordinate system 61.

For example, in the context of FIG. 8B, dots 90-97 represent the edge of the hollow organ 11 via the anchoring of medical tools 41 and therefore various sensing points of optic shape sensor 30 against hollow organ 12. In view of the aforementioned mapping factors, volume mapping may accomplished by connections between dots 90-97 as straight lines and/or arcs (e.g., Bezier curves). As would be appreciated by those having ordinary skill in the art, an increase in dots 90-97 leads to a more accurate volume mapping of the anatomical volume by the image mapper.

Upon completion of stage S83, the volume mapping may be used for a variety of diagnosis and/or treatment purposes. For example, the shape-mapped boundary may be used to define a fixed anatomical volume/feature for multimodality data registration/fusion whereby the shape-tracked instrument space and imaging/monitoring spaces are superimposed allowing for enhanced guidance of the shape-tracked device toward the desired target.

Those having ordinary skill in the art will appreciate how to apply the principles of a volume mapping instrument of the present invention to any type of medical procedure.

Those having ordinary skill in the art will further appreciate the benefits of a volume mapping instrument of the present invention.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A volume mapping instrument deployable within an enclosed anatomical volume for mapping at least a portion of a boundary of the anatomical volume, the volume mapping instrument comprising:
   a medical tool including a medical tube having a helical shape deformable to elongated shape, the medical tube including shape memory material and being transitional between a deployable structural configuration wherein the medical tube has the deformed elongated shape to orderly position the medical tool within the anatomical volume and a mapping structural configuration wherein the medical tube has the helical shape to anchor the medical tube against the boundary of the anatomical volume; and
   an optical shape sensor adjoined to the medical tube, the optical shape sensor being structurally configured to generate at least one encoded optical signal indicative of a shape of the at least a portion of a boundary of the anatomical volume in response to the medical tube being transitioned from the deployable structural configuration to the mapping structural configuration within the anatomical volume.

2. The volume mapping instrument of claim 1, wherein the optical shape sensor is further structurally configured to measure at least one of motion, strain, gas flow, fluid flow, magnetism, voltage, temperature, pressure, and biochemical state.

3. The volume mapping instrument of claim 1, wherein the adjoining of the optical shape sensor to the medical tube includes at least one of the optical shape sensor traversing across the medical tube and the optical shape sensor extending through the medical tube.

4. The volume mapping instrument of claim 1, wherein the optical shape sensor includes at least one optical fiber, each optical fiber structurally configured to generate one of the at least one encoded optical signal indicative of a shape of the at least a portion of a boundary of the anatomical volume in response to the medical tube being transitioned from the deployable structural configuration to the mapping structural configuration within the anatomical volume.

5. A volume mapping system for mapping at least a portion of a boundary of an enclosed anatomical volume, the volume mapping system comprising:
   a volume mapping instrument deployable within an anatomical volume, the volume mapping instrument including:
      a medical tool including a medical tube having a helical shape deformable to an elongated shape, the medical tube including shape memory material and being transitional between a deployable structural configuration wherein the medical tube has the deformed elongated shape to orderly position the medical tool within the anatomical volume and a mapping structural configuration wherein the medical tube has the helical shape in to anchor the medical tube against the boundary of the anatomical volume; and
      an optical shape sensor adjoined to the at least one medical tube, the optical shape sensor being structurally configured to generate at least one encoded optical signal indicative of a shape of the at least a portion of a boundary of the anatomical volume in response to the medical tube being transitioned from the deployable structural configuration to the mapping structural configuration within the anatomical volume; and
   a volume mapping module structurally configured to map the at least a portion of the boundary of the anatomical volume responsive to receiving the at least one encoded optical signal.

6. The volume mapping system of claim 5, wherein the optical shape sensor is further structurally configured to measure at least one of motion, strain, magnetism, voltage, gas flow, fluid flow, temperature, pressure, and biochemical state.

7. The volume mapping system of claim 5, wherein the adjoining of the optical shape sensor to the medical tube includes at least one of the optical shape sensor traversing across the medical tube and the optical shape sensor extending through the medical tube.

8. The volume mapping system of claim 5, wherein the optical shape sensor includes at least one optical fiber, each optical fiber structurally configured to generate one of the at least one encoded optical signal indicative of a shape of the at least a portion of a boundary of the anatomical volume responsive to the medical tube being transitioned from the deployable structural configuration to the mapping structural configuration within the anatomical volume.

9. A volume mapping method, comprising:
providing a volume mapping instrument including a medical tool and an optical shape sensor adjoined to the medical tool to map at least a portion of a boundary of an enclosed anatomical volume,
wherein the medical tool includes a medical tube having a helical shape deformable to an elongated shape, and
wherein the medical tube includes shape memory material and is transitional between a deployable structural configuration wherein the medical tube has the deformed elongated shape and a mapping structural configuration wherein the medical tube has the helical shape;
with the medical tube in the deployable structural configuration, orderly positioning the medical tool within the anatomical volume;
with the medical tube in the mapping configuration, anchoring the helical shape of the medical tube as positioned within the anatomical volume against the boundary of the anatomical volume,
wherein the optical shape sensor senses the anchoring of the medical tube;
in response to the medical tube being anchored against the boundary of the anatomical volume, the optical shape sensor generating at least one encoded optical signal indicative of a shape of the at least a portion of a boundary of the anatomical volume; and
mapping the at least a portion of a boundary of the anatomical volume based on the at least one encoded optical signal.

\* \* \* \* \*